(12) United States Patent
Takats

(10) Patent No.: US 9,709,529 B2
(45) Date of Patent: Jul. 18, 2017

(54) METHOD AND DEVICE FOR IN VIVO DESORPTION IONIZATION OF BIOLOGICAL TISSUE

(71) Applicant: Zoltan Takats, London (GB)

(72) Inventor: Zoltan Takats, London (GB)

(73) Assignee: SEMMELWEIS EGYETEM, Budapest (HU)

( * ) Notice: Subject to any disclaimer, the term of this patent is extended or adjusted under 35 U.S.C. 154(b) by 0 days.

(21) Appl. No.: 13/680,329

(22) Filed: Nov. 19, 2012

(65) Prior Publication Data

US 2013/0224785 A1   Aug. 29, 2013

Related U.S. Application Data

(63) Continuation of application No. 12/302,819, filed as application No. PCT/HU2007/000049 on May 31, 2007, now Pat. No. 8,314,382.

(30) Foreign Application Priority Data

May 31, 2006 (HU) .................................. 0600468

(51) Int. Cl.
  *G01N 27/62* (2006.01)
  *G01N 1/28* (2006.01)
  (Continued)

(52) U.S. Cl.
  CPC ............. *G01N 27/62* (2013.01); *G01N 1/286* (2013.01); *G01N 27/628* (2013.01); *H01J 49/0463* (2013.01); *H01J 49/142* (2013.01)

(58) Field of Classification Search
  CPC .. H01J 49/142; H01J 49/0004; H01J 49/0463; H01J 49/14; H01J 49/165;
  (Continued)

(56) References Cited

U.S. PATENT DOCUMENTS 3,479,545 A   11/1969   Wilson et al.
4,935,624 A   6/1990   Henion et al.
(Continued)

FOREIGN PATENT DOCUMENTS

EP   1 855 306   11/2007
JP   2002-515802   5/2002
(Continued)

OTHER PUBLICATIONS

Smith, D. H., R. W. Olsen, F. C. Walls, and A. L. Burlingame: Real-time mass spectrometry: LOGOS—a generalized mass spectrometry computer system for high and low resolution, gas chromatography/mass spectrometry, and closed-loop applications. Anal. Chem. 43, 1796 (1971)).*

(Continued)

*Primary Examiner* — Brooke Purinton
(74) *Attorney, Agent, or Firm* — Knobbe, Martens, Olson & Bear, LLP

(57) ABSTRACT

The invention relates to method and apparatus for production of gaseous ions from components of a condensed phase sample and analysis thereof, wherein one or more liquid jet(s) is/are directed to the surface of the sample to be investigated, where the impact of the liquid jet on the sample surface produces droplets carrying sample particles which are turned into gaseous ions via the evaporation of liquid or, if desired, by a subsequent ionization after the evaporation and the obtained sample particles are analyzed by a known method.

24 Claims, 8 Drawing Sheets

(51) Int. Cl.
*H01J 49/04* (2006.01)
*H01J 49/14* (2006.01)

(58) Field of Classification Search
CPC .... H01J 49/0468; H01J 49/162; H01J 49/164; A61B 17/3203; A61B 10/02; G01N 2001/045; G01N 2001/2886
USPC .............................. 250/423 R, 281, 282, 288
See application file for complete search history.

(56) References Cited

U.S. PATENT DOCUMENTS

| | | | |
|---|---|---|---|
| 5,559,326 A | 9/1996 | Goodley et al. | |
| 5,841,136 A * | 11/1998 | Holle | H01J 49/0495 250/288 |
| 5,869,344 A | 2/1999 | Linforth et al. | |
| 6,531,318 B1 | 3/2003 | Palmer Toy et al. | |
| 6,825,464 B2 | 11/2004 | De La Mora | |
| 6,838,663 B2 | 1/2005 | Coon et al. | |
| 6,989,528 B2 * | 1/2006 | Schultz | H01J 49/00 250/281 |
| 7,161,144 B2 | 1/2007 | Syage et al. | |
| 7,335,897 B2 | 2/2008 | Takats et al. | |
| 7,564,028 B2 | 7/2009 | Vestal | |
| 7,687,772 B2 | 3/2010 | Shiea | |
| 7,928,364 B2 | 4/2011 | Musselman | |
| 8,203,117 B2 | 6/2012 | Wiseman et al. | |
| 8,207,494 B2 * | 6/2012 | Hieftje | H01J 49/0004 250/281 |
| 8,286,260 B2 | 10/2012 | Vertes et al. | |
| 8,314,382 B2 | 11/2012 | Takáts | |
| 8,324,570 B2 | 12/2012 | Wiseman et al. | |
| 8,395,116 B2 | 3/2013 | Harada et al. | |
| 8,487,244 B2 * | 7/2013 | Vertes | H01J 49/0463 250/281 |
| 9,046,448 B2 | 6/2015 | Takats | |
| 2002/0008871 A1 | 1/2002 | Poustka et al. | |
| 2002/0045911 A1 * | 4/2002 | Fletcher et al. | 606/167 |
| 2002/0070338 A1 * | 6/2002 | Loboda | 250/287 |
| 2002/0076824 A1 | 6/2002 | Haglund, Jr. et al. | |
| 2002/0155483 A1 * | 10/2002 | Holle | H01J 49/40 435/6.12 |
| 2003/0008404 A1 | 1/2003 | Tomita et al. | |
| 2003/0119193 A1 | 6/2003 | Hess et al. | |
| 2003/0193023 A1 | 10/2003 | Marsh | |
| 2004/0007673 A1 | 1/2004 | Coon et al. | |
| 2004/0124352 A1 * | 7/2004 | Kashima et al. | 250/288 |
| 2004/0235395 A1 | 11/2004 | Hashish et al. | |
| 2005/0017091 A1 | 1/2005 | Olsen et al. | |
| 2005/0032471 A1 | 2/2005 | Pfarr et al. | |
| 2005/0072916 A1 | 4/2005 | Park | |
| 2005/0074361 A1 | 4/2005 | Tanoshima et al. | |
| 2005/0077644 A1 | 4/2005 | Bryan et al. | |
| 2005/0138861 A1 * | 6/2005 | O'Connor | 47/41.12 |
| 2005/0154490 A1 | 7/2005 | Blaine et al. | |
| 2005/0159765 A1 | 7/2005 | Moutafis et al. | |
| 2005/0178962 A1 | 8/2005 | Guevremont et al. | |
| 2005/0230635 A1 | 10/2005 | Takats et al. | |
| 2005/0255264 A1 | 11/2005 | Maziers | |
| 2005/0258358 A1 | 11/2005 | Thakur | |
| 2006/0035570 A1 | 2/2006 | Chisum et al. | |
| 2006/0091308 A1 | 5/2006 | Boyle et al. | |
| 2006/0097084 A1 | 5/2006 | Gromer et al. | |
| 2006/0108539 A1 | 5/2006 | Franzen | |
| 2006/0186334 A1 * | 8/2006 | Jolliffe et al. | 250/288 |
| 2006/0229550 A1 * | 10/2006 | Staid et al. | 604/27 |
| 2006/0250138 A1 | 11/2006 | Sparkman et al. | |
| 2006/0255264 A1 | 11/2006 | Belford | |
| 2007/0023631 A1 | 2/2007 | Takats et al. | |
| 2007/0023677 A1 * | 2/2007 | Perkins et al. | 250/425 |
| 2007/0023678 A1 | 2/2007 | Hiraoka | |
| 2007/0094389 A1 | 4/2007 | Nussey et al. | |
| 2007/0110666 A1 | 5/2007 | Pevsner et al. | |
| 2007/0114437 A1 | 5/2007 | Kovtoun | |
| 2007/0176113 A1 | 8/2007 | Shiea et al. | |
| 2007/0224697 A1 * | 9/2007 | Park | 436/173 |
| 2008/0001081 A1 | 1/2008 | Jindai et al. | |
| 2008/0067352 A1 | 3/2008 | Wang | |
| 2008/0149822 A1 | 6/2008 | Vertes et al. | |
| 2008/0172075 A1 | 7/2008 | Ammann | |
| 2008/0173809 A1 | 7/2008 | Wu | |
| 2008/0234579 A1 | 9/2008 | Halevy-Politch et al. | |
| 2008/0262321 A1 | 10/2008 | Erad et al. | |
| 2009/0065714 A1 | 3/2009 | Keady | |
| 2009/0306694 A1 * | 12/2009 | Babaev | 606/169 |
| 2010/0078550 A1 | 4/2010 | Wiseman et al. | |
| 2010/0096546 A1 | 4/2010 | Ewing et al. | |
| 2010/0280409 A1 | 11/2010 | Mark | |
| 2011/0152759 A1 | 6/2011 | Clymer et al. | |
| 2011/0215233 A1 | 9/2011 | Vertes et al. | |
| 2012/0112057 A1 | 5/2012 | Musselman | |
| 2012/0156712 A1 | 6/2012 | Takats | |
| 2013/0082172 A1 | 4/2013 | Syage et al. | |
| 2013/0172916 A1 * | 7/2013 | Bahls et al. | 606/167 |

FOREIGN PATENT DOCUMENTS

| | | |
|---|---|---|
| JP | 2002-536051 | 10/2002 |
| JP | 2004-264043 | 9/2004 |
| JP | 2005-527786 | 9/2005 |
| JP | 2005-539199 | 12/2005 |
| JP | 2007-513695 | 5/2007 |
| JP | 2007-170870 | 7/2007 |
| JP | 2008-147165 | 6/2008 |
| JP | 2009-539093 | 11/2009 |
| JP | 2009-539114 | 11/2009 |
| JP | 2012-505519 | 3/2012 |
| WO | WO 85/04093 | 9/1985 |
| WO | WO 2005/083415 | 9/2005 |
| WO | WO 2005/094389 | 10/2005 |
| WO | WO 2006/081240 | 8/2006 |
| WO | WO 2007/138371 A2 | 12/2007 |
| WO | WO 2007/140351 A2 | 12/2007 |
| WO | WO 2009/157312 A1 | 12/2009 |
| WO | WO 2010/136887 | 12/2010 |
| WO | WO 2012/061143 | 5/2012 |
| WO | WO 2012/164312 | 12/2012 |

OTHER PUBLICATIONS

Down, S., "A DESI-rable ionization revolutionizes mass spectrometry", Base Peak, Aug. 15, 2005.

Takats, Z. et al., "Mass spectrometry Sampling under Ambient Conditions with Desorption Electrospray Ionization", Science, Oct. 15, 2004, vol. 306.

English Translation of Japanese Office Action, Japanese Patent Application No. 2012-512467, mailing date: Nov. 5, 2013.

International Search Report, for International Application No. PCT/IB2012/002995, date of mailing: Sep. 10, 2013 (3 pages).

Written Opinion of the International Searching Authority, for International Application No. PCT/IB2012/002995, date of mailing: Sep. 10, 2013 (6 pages).

Cooks, R. Graham, et al. "Ambient mass spectrometry." Science 311.5767 (2006): 1566-1570.

English Translation of Japanese Office Action, Japanese Patent Application No. 2014-041012, mailed Feb. 17, 2015.

Al Sahaf, O. S., et al. "Chemical composition of smoke produced by high-frequency electrosurgery." Irish journal of medical science 176.3 (2007): 229-232.

Barrett, William L., and Shawn M. Garber. "Surgical smoke: a review of the literature." Surgical endoscopy 17.6 (2003): 979-987.

Choy, D. S. "History of lasers in medicine." The Thoracic and cardiovascular surgeon 36 (1988): 114-117.

Lee et al., "Thermally Assisted Electrospray Interface for Liquid Chromatography/Mass Spectrometry," Rapid Commun. Mass Spectrom. 1992, 6:727-733.

Mathey, Annick, Luc Van Vaeck, and Wolfgang Steglich. "Investigation of semi-thin cryosections of lichens by laser microprobe mass spectrometry." Analytica chimica acta 195 (1987): 89-96.

(56) References Cited

OTHER PUBLICATIONS

McEwen et al., "Analysis of Solids, Liquids, and Biological Tissues Using Solids Probe Introduction at Atmospheric Pressure on Commercial LC/MS Instruments," Anal. Chem. 2005, 77:7826-7831.

Moot, et al. "Composition of Volatile Organic Compounds in Ion Flow Tube Mass Spectrometry," ANZ Journal of Surgery, 2007, vol. 77, pp. 20-23 in 4 pages.

Sakairi et al., "Characteristics of a Liquid Chromatograph/Atmospheric Pressure Ionization Mass Spectrometer," Anal. Chem. 1988, 60:774-780.

Spengler, B., et al. "Laser mass analysis in biology." Berichte der Bunsengesellschaft für physikalische Chemie 93.3 (1989): 396-402.

Takats et al., "Characterization of DESI-FTICR mass spectrometry—from ECD to accurate mass tissue analysis," J. Mass Spectrom. 2008, 43:196-203, published online Oct. 8, 2007.

Tottszer et al., "laser heating versus resistive heating in the field-desorption mass spectrometry of organic polymers," J. Phys. D: Appl. Phys. 1988, 21:1713-1720.

Van Vaeck, L., and R. Gijbels. "Laser microprobe mass spectrometry: potential and limitations for inorganic and organic microanalysis—Part I." Fresenius' Journal of Analytical Chemistry 337.7 (1990): 743-754.

Van Vaeck, L., and R. Gijbels. "Laser microprobe mass spectrometry: potential and limitations for inorganic and organic microanalysis—Part II." Fresenius' Journal of Analytical Chemistry 337.7 (1990): 755-765.

Verbueken, A. H., et al. "Identification of inorganic and organic microliths in kidney sections by laser microprobe mass spectrometry." Analytica chimica acta 195 (1987): 97-115.

Liang Qiao et al., "Electrostatic-Spray Ionization Mass Spectrometry," *Analytical Chemistry*, vol. 84, No. 17, Sep. 4, 2012, pp. 7422-7430.

\* cited by examiner

METHOD AND DEVICE FOR IN VIVO DESORPTION IONIZATION OF BIOLOGICAL TISSUE

CROSS-REFERENCE TO RELATED APPLICATIONS

This application is a continuation of U.S. application Ser. No. 12/302,819, filed Aug. 13, 2009, which is the U.S. national stage of International Application No. PCT/HU2007/000049, filed May 31, 2007, which claims priority to Hungarian patent application serial no. P0600468. The entirety of the contents of each of these applications is hereby incorporated by reference.

BACKGROUND OF THE INVENTION

Field of the Invention

The subject of the invention is a method and apparatus for converting components of a condensed phase sample into gaseous ions and analysis thereof.

During the implementation of the method according to the invention a high-velocity liquid jet is impacted with the surface of said sample. The liquid droplets formed at the impact of the liquid with the surface of the sample carry away the components of the sample (desorption step). The sample remaining after the evaporation of the solvent is a gaseous ion itself or it is convertible into gaseous ion by the use of an external effect—heat, electromagnetic effect etc. (optional step for providing gaseous ions). The obtained gaseous ions are analyzed, preferably by mass spectrometry or ion mobility spectrometry (detection step).

Description of the Related Art

Mass spectrometric ionization methods have been traditionally developed for the analysis of gaseous or volatile materials. Disadvantage of these ionization methods is that they lack the capability of analysis of non-volatile compounds. This group of compounds includes e.g. peptides, proteins, nucleic acids, carbohydrates. From the 1970's a new family of ionization methods has been developed which was able to convert condensed phase molecules directly into ions on the gas/solid interface and subsequently transfer the nascent ions to the gas phase. These ionization methods are generally named as "desorption ionization" methods since they are coupled with the desorption of the formed ions. First desorption ionization method was the so-called field desorption ionization generated by electric field, which utilizes the high electric field gradient formed around the edges of sharp surface features for the parallel ionization and desorption of the molecules present on surface. [Beckey, H. D., Organic Mass Spectrometry 6 (6), 6558-(1972)]. The disadvantage of this method is that the sample has to be deposited onto the very edge of emitter needles and the geometry of emitter tips has a strong influence on ionization efficiency.

The next generation of desorption ionization methods are based on an alternative way of ionization by utilizing a so-called analytical beam for ionization. In this method a beam comprising high energy ions, atoms or photons is impacted with the surface of the studied sample. Impact of analytical beam on surface produces some gaseous ions and molecules deriving from the studied surface. First method utilizing analytical beam was plasma desorption ionization which employed high energy particles produced by radioactive decay [Macfarlane, R. D. et al., Science, 191 (4230), 920-925 (1976)].

While in case of plasma desorption a poorly defined beam was utilized, secondary ion mass spectrometry (SIMS), which was developed practically at the same time, employed a well-defined analytical beam of ions accelerated by electric potential difference [Bennighoven, A., Surface Science 28(2) 541-(1971)]. SIMS provides an excellent spatial resolution, due to the small diameter of ion beams, but the molecular weight range of molecules, which undergo SIMS ionization, is limited. Method can also be used for in-depth analysis, however, in this case the molecular weight limits are more critical since the formed ions contain only 1 or 2 atoms. Study of liquid samples was developed first time in the case of SIMS ionization [liquid SIMS; LSIMS, Aberth, W., Analytical Chemistry, 54 (12): 2029-2034 (1982)]. LSIMS has softer range limits compared to the original method, e.g. small protein molecules can be ionized by it. Disadvantage of LSIMS is that the samples have to be dissolved in a solvent having high surface tension and low vapour pressure such as glycerol. This step often involves solubility problems, and dissolution of solid samples obviously excludes the possibility to obtain information about spatial distribution of the molecules of a sample.

A further developed version of LSIMS is the "fast atom bombardment" (FAB) method [Williams, D. H. et al., JACS, 103 (19): 5700-5704 (1981)]. The technique is based on the electrostatic acceleration of noble gas ions followed by neutralization, yielding a neutral beam of nobel gas atoms having yet a high energy level which can be utilized for ionization. FAB ionization is also suitable for the analysis of liquid phase samples.

Another direction of development of SIMS technique has led to the so-called massive cluster impact (MCI) ionization [Massive cluster impact; MCI, Mahoney, J. F., Rapid Communications in Mass Spectrometry, 5 (10): 441-445 (1991)] which utilizes multiply charged glycerol clusters instead of the traditionally applied gold ions. This technique can be applied for the analysis of solid surfaces and the weight of the analyzed molecules is not limited practically. A further advantage of this technique is, compared to SIMS, that multiply charged ions are formed which can be analyzed more effectively by mass spectrometry.

Common disadvantage of described methods is that all of them work strictly under high vacuum conditions. Hence, samples are introduced into high vacuum regime of mass spectrometers, which involves strong restrictions on the composition and size of samples.

Laser desorption ionization methods, where laser was applied as analytical beam, have been developed from the early 1980's [Cooks, R. G. et al., JACS, 103 (5): 1295-1297 (1981)]. Simple laser desorption ionization, similarly to SIMS, gives poor ionization efficiencies and they can only be used for the study of a very limited scope of molecules. Application area of laser desorption methods was dramatically extended by the application of so-called matrix compounds. Matrix compounds, which are present in great excess, are generally mixed to sample in solution phase and the mixture is co-crystallized onto solid carrier and the obtained crystallized sample is analyzed by means of laser desorption, i.e. where laser is used as an analytical beam. The new method was named as matrix-assisted laser desorption ionization (MALDI) [Karas, Hillenkamp, Analytical Chemistry, 60 (20): 2299-2301 (1988)]. The technique can be applied generally for the analysis of macromolecular compounds such as polymers, proteins, carbohydrates and nucleic acids. Main disadvantage of MALDI is that the technique requires embedding of analyte molecules into matrix crystal lattice, thus analysis of natural surfaces is problematic.

Need for desorption ionization methods working under atmospheric conditions has been raised recently. Advantages of atmospheric pressure desorption ionization method include: (1) samples are not introduced into vacuum regime of mass spectrometer, which makes the analytical procedure faster, (2) since sample does not enter vacuum, there is no need for the removal of volatile components, (3) arbitrary objects can be investigated this way, (4) living organisms can be studied directly. Desorption ionization methods utilizing high-velocity beam of atoms or ions cannot be used under atmospheric pressure conditions, since particles cannot be accelerated to suitable velocities at high pressure due to consecutive collisions with gas molecules and this phenomenon is responsible for the divergence of particle beams.

Among the above described methods, only the MALDI ionization can be implemented at atmospheric pressure without changes in instrumentation since laser beams do not interact with air molecules. Atmospheric pressure MALDI was developed by Laiko et al. in 2002. However, the technique did not spread widely due to low ion yield which is further decreased by the substantial ion loss in the atmospheric interface, and workplace safety issues generally associated with the use of laser in open experimental setups.

The recently developed desorption electrospray ionization (DESI; Takats et al., Science, 306 (5695): 471-471, 2004) is practically the atmospheric pressure version of MCI technique described above, but having the important difference that the droplets are produced by electrospray method and accelerated to the desired velocity by supersonic gas stream instead of electrostatic field gradient. Nevertheless, DESI has fulfilled all expectations associated with atmospheric pressure desorption ionization methods, so it opened the door to the mass spectrometric analysis of arbitrary objects independently from their chemical composition and size. In the course of DESI process, high-velocity electrosprayed droplets impact with sample surface. Impacting droplets dissolve molecules present on surface and emit secondary droplets which are also charged. These charged secondary droplets produce ions finally via complete evaporation of solvent.

Although DESI technology bears a number of advantages compared to previously developed desorption methods, it also shows drawbacks on several fields of applications. At first, DESI is a strict surface analysis method, thus it lacks the capability of in-depth analysis in case of most samples. At second, since the atmospheric pressure beam of charged droplets is intrinsically divergent due to Coulomb repulsion among charged particles, it hinders the high-resolution chemical imaging. Furthermore, although DESI is fully compatible with biological tissues from analytical point of view, in vivo application of DESI was shown to cause embolism in various animal models. Embolism was tentatively associated with the supersonic nitrogen stream applied for the acceleration of the droplets, which pumps gas bubbles into the tissue and causes embolism.

In order to provide solution for the above listed problems, a need has emerged for an alternative atmospheric pressure desorption ionization method which employs collimated and high-energy analytical beam where the beam is not constituted by droplets accelerated by high-velocity gas. The aim of our research was to develop an atmospheric pressure ionization method which is capable of in-depth analysis of samples, high-resolution chemical imaging and in-vivo analysis.

SUMMARY OF THE INVENTION

As a result of our research work, a new method and apparatus was developed which is working at atmospheric pressure, wherein a high-velocity, continuous liquid jet is applied as analytical beam which, preferably, carries electrical charge. It has to be noted that ion formation may still occur in case of a liquid beam without charge, but the impact of the liquid jet can result in much higher number of charged particles if the liquid jet itself has charged particles. Positive electric potential generates positively charged ions, while negative potential generates negatively charged ions.

Invention is based on the recognition that a liquid jet (which can be any liquid, e.g. water, aqueous solution, other polar solvent or any mixture of them) having enough energy is able to dislocate particles from the sample, ensuring by it the possibility of in-depth analysis. A further advantage of the method is hidden in the fact that said high-velocity liquid jet is less divergent, thus enables chemical imaging with micrometer scale resolution, moreover, the method is applicable for in-vivo study of biological systems.

Subject of invention is a method for converting certain components of a condensed phase sample into gaseous ions and analysis thereof, wherein ions or sample particles convertible into ions are dislocated from the sample by an analytical beam released from a desorption unit, and the obtained gaseous ions are analyzed, comprising:

applying a liquid jet as analytical beam, evaporating or allowing to be evaporated the liquid of the droplets which are formed when the liquid hit the surface and, if desired, the liquid droplets or the sample particles obtained by the evaporation of the liquid are ionized before said analysis.

The analysis is performed by known methods which differentiate components of the sample on the basis of the charge, size, mass or other characteristic of the sample ions. Preferably mass spectrometric or ion mobility spectrometric analysis is applied.

Preferred embodiments of the invention are as follows:

Method wherein water, an aqueous solution or any other polar solvent or any mixture thereof is applied as the liquid component of said liquid jet.

Method wherein potential difference is applied between said analyser unit and the equipotential said liquid jet and sample. It has to be emphasized that in the above preferred embodiment said sample is equipotential to liquid jet as said liquid jet is preferably a conductive liquid, e.g. water.

Method wherein mass spectrometer or ion mobility spectrometer is applied as said analyser unit.

Method wherein obtained said gaseous ions are transferred to said analyser unit through a sample collector unit designed for this purpose.

Method wherein said droplets or dislocated sample particles are ionized between said analyser unit and sample.

Method wherein said sample is deposited on a surface prior to analysis.

Method, wherein the temperature of said sample is controlled externally by cooling or heating.

Method, wherein the excess liquid originated from said liquid jet and non-transferred to said analyser unit is removed by suction during the method.

Method, wherein a high-velocity gas mantle is generated around said liquid jet, decreasing by it the friction and divergence of the liquid jet.

Method, wherein multiple liquid jets are applied.

Method, wherein one or more said desorption unit/s is/are moved relatively to said sample in order to determine the spatial distribution of the composition of said sample.

Method, wherein said sample is moved relatively to one or more said desorption unit/s in order to determine the spatial distribution of the composition of said sample.

Method, said liquid jet is used to cut into said sample in order to determine the in-depth distribution of the composition of said sample.

Method, wherein the said sample is biological tissue.

Method, wherein said sample is exposed by any known surgery method.

Method, wherein said droplets and sample particles formed at the interaction of said liquid jet and said sample are transferred to said analyser unit by gas streaming method, if desired, after ionization.

Method, wherein a compound is mixed into said liquid jet which reacts with specific components of said sample.

Method, which is carried out under pressure conditions being different from atmospheric.

Further subject of invention is an apparatus for converting components of a condensed phase sample into gaseous ions, comprising
- a 5 surface for carrying a 6 sample,
- at least one A desorption unit for dislocating ions or 8 sample particles convertible into ions from 6 sample,
- 9 sample collector unit,
- 10 analyser unit, characterized in that said A desorption unit has a 3 nozzle providing a 1 liquid jet, a 2B tube for transferring 2 liquid, said tube is connected to said 3 nozzle, and said 3 nozzle is directed to said 5 surface for carrying said 6 sample.

Preferred embodiments of said apparatus are as follows:

Apparatus wherein said liquid jet is water, an aqueous solution or any other polar solvent or any mixture thereof.

Apparatus comprising a 4 device for generating electric potential difference between said 1 liquid jet and said 5 surface. It has to be noted that in a preferred embodiment the said sample is equipotential to liquid jet as said liquid jet is preferably a conductive liquid, e.g. water.

Apparatus wherein said 10 analyser unit is a mass spectrometer or ion mobility spectrometer.

Apparatus wherein the 9A outlet of said 9 sample collector unit is placed into close proximity of 5 surface.

Apparatus wherein a 2 unit for evaporation of said liquid is placed between said 5 surface and said 10 analyser unit.

Apparatus wherein a 8 unit for ionization of sample particles is placed between said 5 surface and said 10 analyser unit.

Apparatus wherein at least one A desorption unit has a position controller relative to said 6 sample, or said 5 surface for carrying said 6 sample has a position controller relative to said A desorption unit providing the possibility of movement of 6 sample relative to A desorption unit.

Further subject of invention is an apparatus for converting components of a condensed phase sample into gaseous ions, which can be used for hollowing a cavity into a sample or for cutting a sample, comprising
- at least one A desorption unit for dislocating ions or 8 sample particles convertible into ions from 6 sample,
- 20 tube which is a part of 9 sample collector and is connected to analyser unit, characterized in that said A desorption unit has a 3 nozzle providing the 1 liquid jet, a 2B tube for transferring 2 liquid, said tube is connected to the 3 nozzle, and said A desorption unit and said 20 tube connected to analyser unit are fastened to each other by a 19 holder.

Preferred embodiments of the apparatus are as follows:

Apparatus wherein said liquid is water, an aqueous solution or any other polar solvent or any mixture thereof.

Apparatus comprising a 4 device for generating electric potential difference between said 1 liquid jet and said 20 tube connected to analyser unit. It has to be noted that in a preferred embodiment the said sample is equipotential to liquid jet as said liquid jet is preferably a conductive liquid, e.g. water.

Apparatus, wherein the 20A outlet of the 20 tube connected to analyser unit is placed into close proximity of said 3 nozzle. It has to be noted that droplets and sample particles generated by the impact of the said liquid jet and said sample can be transferred to the said analyser unit not only by potential difference, but by viscous gas stream (suction or blow), too, preferably after ionization.

Apparatus, wherein said 9 sample collector unit or said 20 tube connected to analyser unit comprises 21 heater and 22 thermometer.

Apparatus, wherein said 9 sample collector unit or said 20 tube connected to analyser unit comprises a device for the ionization of the 8 sample particles.

Application of apparatus and method according to the present invention is especially preferred when components of sample cannot be directly transferred into gas phase or when temperature of sample cannot be elevated without undesired chemical changes or when the aim of the study is to determine spatial distribution of the concentrations of analyzed components.

DETAILED DESCRIPTION OF THE PREFERRED EMBODIMENT

The important elements of the above definitions are given in details below. The non-defined other elements (e.g. emission, component) are applied in usual meaning being obvious for a skilled person in the field.

1. Condensed Phase Samples

Method and apparatus described herein ("method according to the invention" in the followings) can be used for the analysis of arbitrary solid or liquid material containing components which can be ionized to form gas phase ions. Samples can have homogeneous or arbitrarily heterogeneous structure (e.g. human or animal tissues, bone, wood etc.).

Method according to the invention can be advantageously used for the analysis of samples deposited and dried from solutions, preferably biological samples where the analysis is carried out for medical diagnostic or pharmacological purposes. Examples for such biological samples are fluids, i.e. blood, urine, liquor etc.) Obviously, extracts of arbitrary samples can also be studied this way.

The other application area of key importance is the study of natural objects (where the actual object serves as sample) wherein the natural object can be chosen arbitrarily (e.g. soil, rock, foodstuffs, living tissues). Further important areas of applications are as follows:

study of metabolic processes of living tissues, determination of spatial distribution of drug molecules (or peptides, lipids etc.) in living biological tissues, e.g. in brain, gaining information during surgery about the tissue being cut (e.g. whether it contains cancer cells or not) to increase the efficiency of tissue removal and to minimize the overall mass of removed healthy tissue, investigation of wood objects in order to detect organic (e.g. fungal) or inorganic (e.g. antifungal agents) contamination, determination of consumed materials (drugs of abuse, alcohol, medicines, coffee, nicotine etc.) from skin, analysis of soil samples, e.g. in on-field studies (for environmental pollutants and bacterial or fungal biomarkers), determination of fitness for consumption of human and animal foodstuffs and level of undesired chemical agents (e.g. antibiotics), determination of spatial distribution of elemental composition of arbitrary objects, preferably in combination with ICP-MS method.

2. Liquid Jet/Liquid

In the method according to the present invention every suitable liquid can be applied theoretically as the liquid of the liquid jet, but preferably a conductive liquid is applied, which can be water, aqueous solutions, solvent systems containing water, any polar solvents (methanol, ethanol, dimethyl-formamide, dimethyl-sulfoxide, acetonitrile etc.), mixtures of them which contain preferably additives undergoing ionic dissociation in these solvents, e.g. acetic acid, formic acid, tetramethylammonium bromide etc. Among all solvent systems water is highly preferred.

Further requirement on liquid used is to have sufficiently high surface tension in order to hinder the disruption of jet into droplets.

Liquid may contain compounds which undergo chemical reaction with the sample. Liquid can also be a suspension, which is especially preferred in the case of in-depth analysis.

3. Desorption Unit

Desorption unit is capable to emit continuous liquid with appropriate velocity, diameter and pressure into appropriate direction and "sampling from the sample". Preferably the desorption unit is a 2B or 11 tube ending in 3 nozzle.

In a preferred embodiment of the method according to the invention the liquid is forced through a nozzle with diameter in the range of 1 to 100 µm, preferably 1 to 60 µm, more preferably 1 to 5 µm at pressures in the range of 50 to 1500 bar, preferably 100 to 1000 bar, more preferably 200 to 600 bar.

4. Desorption and Ionization of Particles

When the liquid jet is impacted with the sample then droplets are formed which carry away particles of the sample (sample particles).

The electrically charged droplets produce gaseous ions as solvent evaporates.

Droplets may be charged on formation or can be ionized in a later step, either by the use of strong electric potential gradient, or by impacting them with other charged liquid droplets, or by photoionization, or by plasma (e.g. by Inductively Coupled Plasma, ICP). While in the first three cases the ionized droplets produce molecular ions, in the latter case atomic ions are formed. Accordingly, in the first three cases analytical information can be obtained mainly on molecular level, while in the latter case the elemental composition can be determined.

Since the electric potential of liquid jet facilitates the charging of said droplets or particles on formation, preferably electric potential gradient is established between electrically conductive liquid jet and ground potential by applying high voltage between liquid jet and ground in the range of 1 to 8 kV, preferably 2 to 6 kV, more preferably 4 to 5 kV.

5. Evaporation

Since gaseous ions should be transferred to the analyser unit, liquid have to be fully evaporated from the droplets previously. This may occur on natural way (i.e. the liquid evaporates at the applied temperature), or it can be facilitated by implementation of a device which accelerates the evaporation (e.g. heater or high temperature gas stream).

6. Analyzer Unit

Analyzer unit is capable of detecting ions, thus the analyser unit is preferably a mass spectrometer or an ion mobility spectrometer.

Sample Collector Unit

Gaseous ions produced by the method are transferred into the analyser unit by using sample collector unit (which is preferably a tube in which pressure difference is generated). This applies only if the steps above are not carried out directly in the analyser unit (the latter is a preferred embodiment, see below).

8. Surface for Carrying the Sample

The surface applicable for carrying the sample is preferably an electrically insulating surface which can resist the applied liquid jet. Sample carrier is preferably made of plexiglass, glass, ceramics or quartz. If the sample carrier surface is electrically conductive, then potential difference needs to be generated between the surface and the inlet of the analyser unit by means of a suitable electric power supply.

Additional Preferred Embodiments

1. In this embodiment a high-velocity, electrically charged continuous liquid jet is applied as analytical beam. As the liquid jet impacts the surface, liquid is accumulated on the surface and said liquid is removed continuously through a tube system located near the impact area, assisted by vacuum. This setup eliminates surface cross-contamination caused by occasional liquid accumulation, i.e. the transfer of analyte molecules by the accumulated liquid phase to locations where they were not present previously.

2. In this embodiment the analyzed sample and/or the liquid jet nozzle is mounted on a carrier stage allowing a three-dimensional (3D) movement. This instrumental setup is able to provide position dependent information on the chemical composition of the sample.

3. In this embodiment the point of impact on the surface and impact angle are controlled. Controlled movement of point of impact on surface is implemented by 3D linear moving carrier stage to control the position of sample and the nozzle emitting the liquid relative to each other. Impact angle of liquid jet is controlled by rotating either the sample or the nozzle with the desired angle by the use of a rotating carrier stage.

4. In this embodiment the electric potential gradient necessary for ion formation is established by electrically connecting the outlet of a high voltage power supply and the electrically conductive liquid jet used as analytical beam, and the desorption unit is used as counter electrode.

5. In this embodiment the liquid jet is kept at or close to ground potential (<150 V), and the sample collector unit is kept at high electric potential (>1000 V) having opposite polarity relative to the polarity of ions generated.

6. In this embodiment the liquid jet is kept at high electric potential relative to the inlet of sample collector unit and said liquid jet is surrounded by high-velocity gas jet. Embodiment extenuates jet deceleration and also prevents the increase of jet diameter at atmospheric pressure.

7. In this embodiment the liquid jet is kept at high electric potential relative to the inlet of the sample collector unit and the temperature of stage carrying the sample is controlled in the range of −50 to +300° C. Advantage of this embodiment is that samples which are liquid or soft at ambient temperature can be solidified for the analysis at lowered temperature. Further advantage of this embodiment is that the ionization efficiency of certain components can be enhanced at higher temperatures.

8. In this embodiment multiple continuous liquid jets are applied for ionization, which are kept at high electric potential relative to the inlet of the sample collector unit. Advantage of this embodiment is that larger surface can be investigated this way and also higher ion current is achievable.

9. In this embodiment the liquid jet contains compounds undergoing prompt chemical reactions with certain components of the sample. In certain cases the products of said chemical reaction are analyzed, while in other cases the chemical reaction is utilized to suppress the undesired ionization of components.

10. In this embodiment decreased pressures (p<1 bar) is applied. In this case the formed ions need not to be transferred through atmospheric interface to the mass spectrometer causing a great ion loss, since the ionization can be made in the vacuum chamber of mass spectrometer.

11. In a further preferred embodiment the liquid jet is used for cutting into the sample (i.e. the liquid jet is applied as a cutting device). This embodiment provides real-time information on the chemical composition of object being cut. Droplets formed on the disruption of liquid jet are electrically charged by travelling through electric potential gradient and mass spectrometry is used for the analysis of ions formed. The electric potential difference is established between the sample to be cut and the mass spectrometer by using high-voltage electric power supply.

12. In a further preferred embodiment a known surgical tool (electric surgery tool, scalpel, laser etc.) is used to cut into sample and the parts of sample exposed this way are analyzed using method described above. This way the combination of the known surgical method and the method according to the present invention provides information continuously on the composition of sample being cut by conducting the droplets formed from said liquid and said sample through an electric potential gradient and analyzing the resulting gaseous ions by mass spectrometry. Potential gradient is established between sample and mass spectrometer by using high-voltage electric power supply. In an other embodiment said droplets and particles of sample can also be transferred to analyser unit by using gas streams (blow or suction), preferably following ionization step.

DESCRIPTION OF THE DRAWINGS

Drawings are not scaled; their purpose is the demonstration of preferred embodiments of invention. Same numbers refer to identical structural elements.

FIG. 1 demonstrates the working concept of the apparatus according to the invention. During the embodiment of the method according to the present invention a high-velocity 1 liquid jet is generated by pumping electrically conductive 2 liquid through 3 nozzle. 2 liquid is transferred to 3 nozzle through 2B tube. Potential difference is generated in the order of several kilovolts between ground and 1 liquid jet by using high-voltage 4 power supply. 1 liquid jet, directed onto 5 surface, produces 7 liquid droplets, that are electrically charged if 5 surface is insulator, or conductive but electrically isolated from ground. Electrically charged 7 droplets contain particles (e.g. molecules) of 6 sample deposited onto 5 surface which are soluble in 2 liquid. Evaporation of 2 solvent from electrically charged 7 droplets leads to the formation of gaseous 8 ions of components of 6 sample being soluble in 2 liquid that can be transferred into 10 analyser unit (which is preferably mass spectrometer where the ions can be analyzed by mass spectrometric method) through 9 sample collector unit (preferably atmospheric interface). By this method information can be gathered about 5 surface, or if 5 surface is inert, then about 6 sample deposited onto 5 surface.

FIG. 2 depicts a preferred embodiment of apparatus in accordance with the invention. Electrically conductive 2 liquid, for example 0.1 mM aqueous HCl solution, is pumped through stainless steel 11 tube at pressure of 50 to 1500 bars. High electric potential of 1 to 8 kV is generated between 2 liquid and ground by connecting high-voltage 4 power supply to stainless steel 11 tube. 2 liquid is emitted from 11 tube through 15 stainless steel or sapphire nozzle which is held by 12 stainless steel connector, 13 stainless steel seals and 14 screwed holder having no screw, with linear velocity of 100 to 1000 m/s. Stainless steel 11 tube is mounted on a rotational and three dimensional linear moving stage through 12 screwed holder. Motion system provides proper control on the relative position of 3 nozzle, 6 sample and 9 sample collector unit, and also on 15 impact angle and 16 collection angle. Optimal distance between 3 nozzle and 5 surface is in the range of 1 to 20 mm, optimal 15 impact angle is in the range of 60 of 90 degrees. Excess liquid accumulating occasionally on surface is removed by 17 drain tube, the far end of which is connected to a pump.

FIG. 3 depicts the preferred embodiment of apparatus in accordance with invention described in Example 2. Differently from FIG. 2, 3 nozzle is created by sealing the end of 1/16" outer diameter stainless steel 11 tube by welding, and a 0.2 mm long hole having a diameter of 1 μm is drilled into end wall by means of laser drilling. 1 liquid jet is moved in parallel with surface of 6 sample in order to abrade 18 surface in depth, while the certain components of eroded surface material being soluble in the applied liquid are transformed into gaseous 8 ions which are transferred to mass spectrometer by 9 unit. Polyethylene 17 drain tube is applied to remove excess liquid accumulating on surface with the aid of a suitable pump.

FIG. 4 depicts a preferred embodiment of apparatus in accordance with invention described in details in Example 3. Apparatus of FIG. 4, differently from FIGS. 2 and 3, comprises 3 nozzle made of fused silica which was made by using capillary puller device. Fused silica 3 nozzle, similarly to the embodiment given on FIG. 2, is connected to stainless steel 11 tube by 13 connector. Differently from embodiments depicted on FIGS. 2 and 3, ions are not collected directly by the atmospheric interface of mass spectrometer, but by using 1 m long, 1/8" outer diameter, 2 mm internal diameter, copper 20 tube connected to the analyser unit (mass spectrometer). Copper 20 tube is heated by 21 heater which is controlled by using the temperature feedback from 22 thermometer.

This apparatus does not comprise 5 surface, since primary function of it is direct sampling of objects and can be used as a surgical cutting device, too. Fastening of the elements of the apparatus is ensured by 19 holder.

Figure 1:
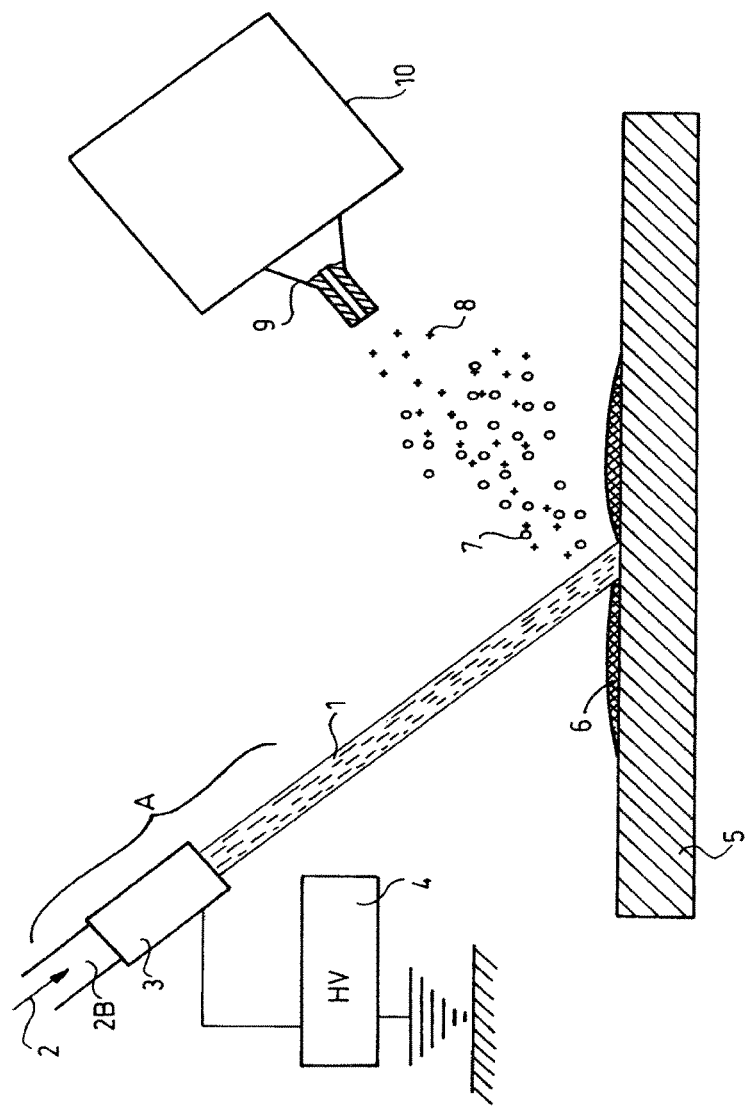
FIG. 1 demonstrates the working concept of invention.
Figure 2:
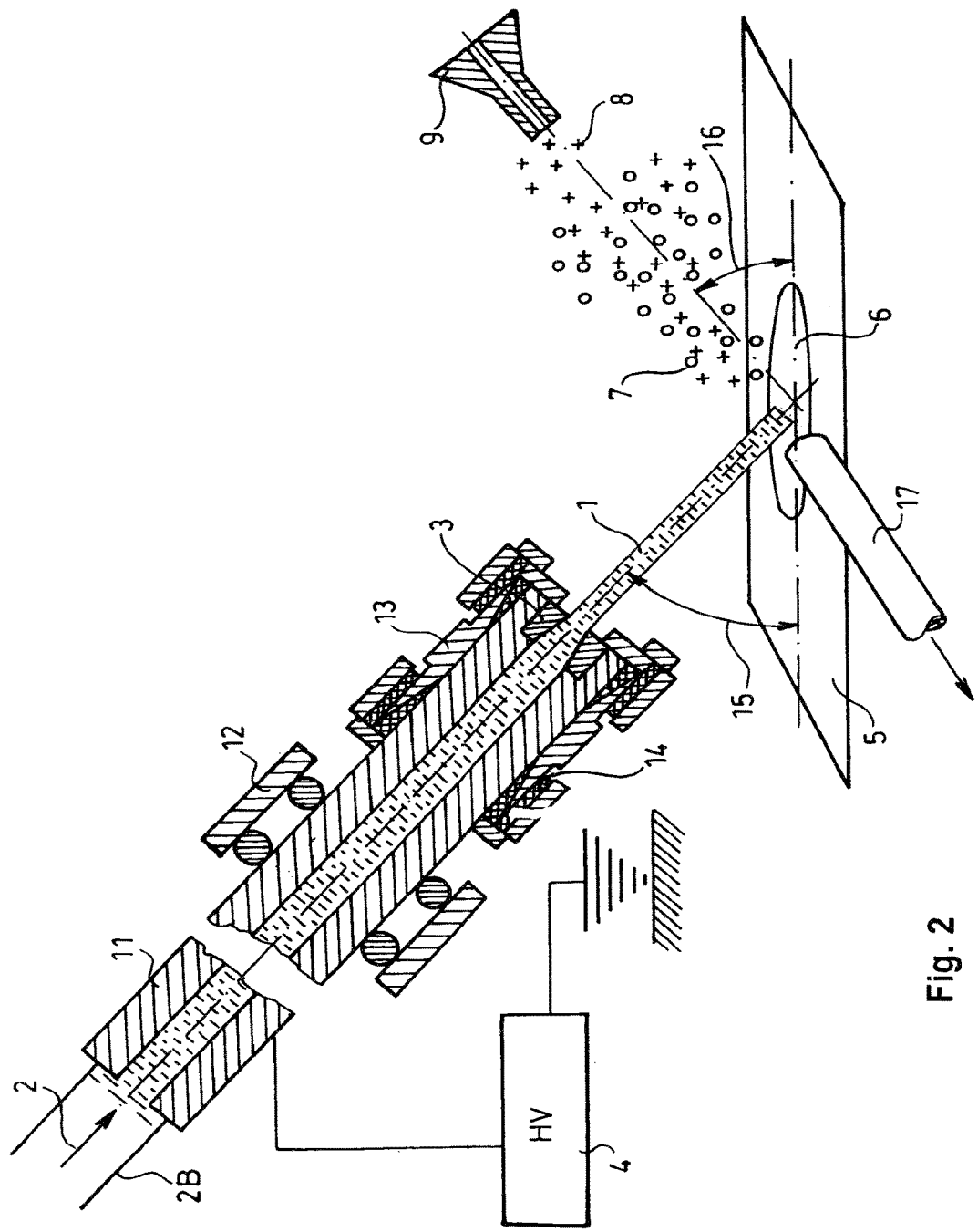
FIGS. 2, 3 and 4 depict three different embodiments of invention.
Figure 3:
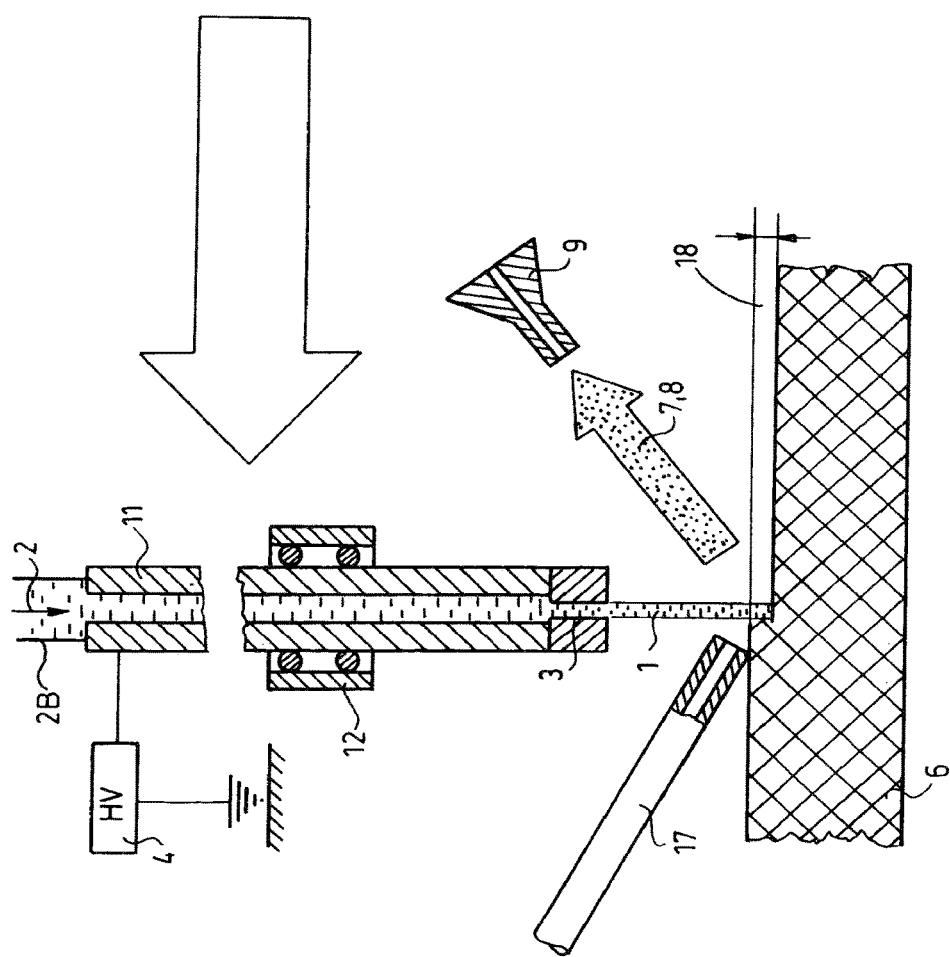
Figure 4:
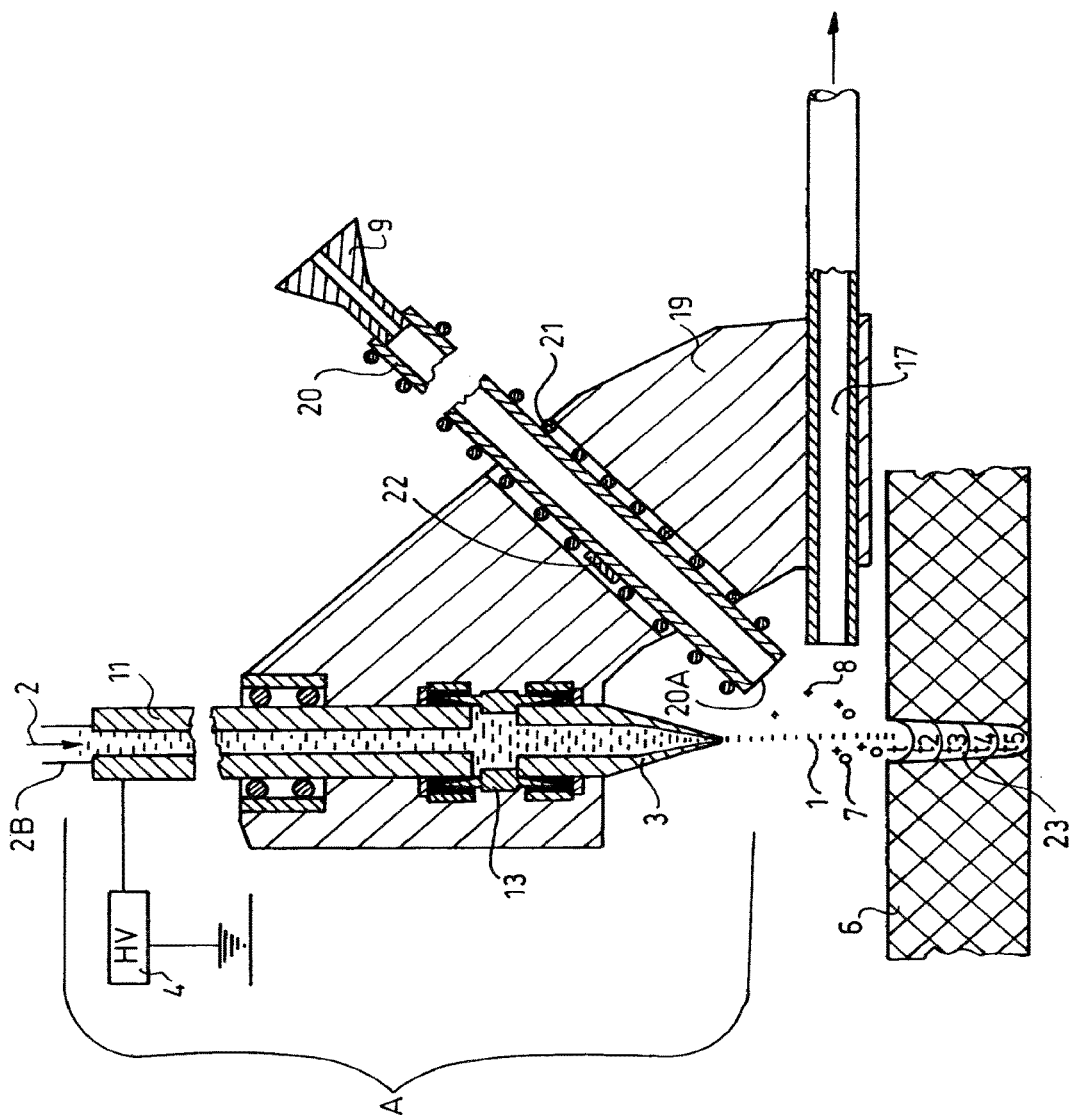

Similarly to the embodiments of FIGS. 2 and 3, also a polyethylene 17 drain tube is applied to remove excess liquid accumulating occasionally on the surface. Relative position of the elements of the apparatus is provided by 19 holder. The aim of apparatus as visible on FIG. 4 is not the analysis of the surface of 6 sample, but cutting of 6 sample by 23 method and gathering of chemical information about the composition of sample being cut.

Figure 5:
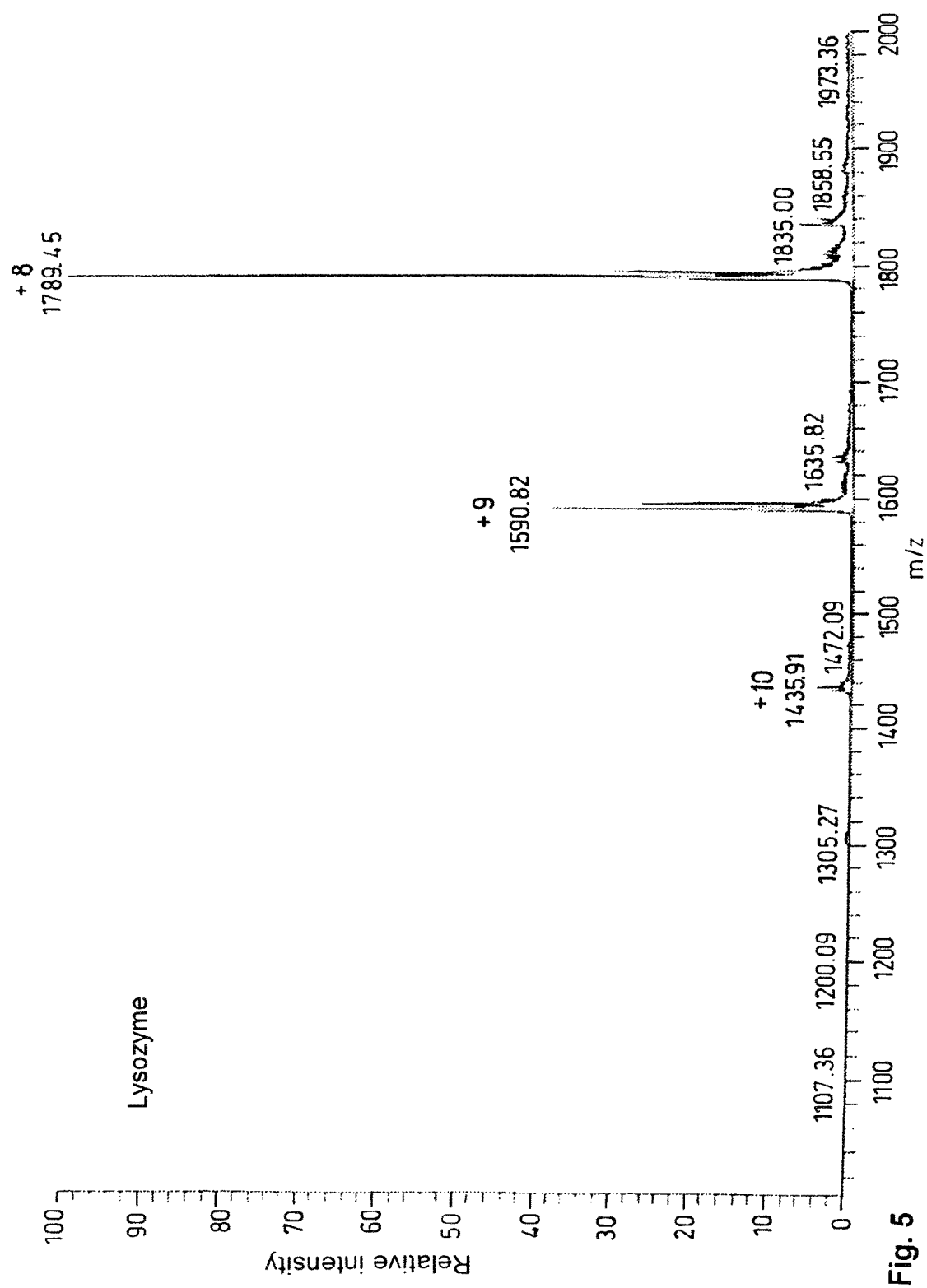
FIGS. 5, 6, 7, and 8 are mass spectra obtained by using the apparatus.

FIG. 5 shows the mass spectrum obtained by apparatus depicted on FIG. 2. 10 μl aqueous solution containing 100 ng hen egg-white lysozyme was deposited and dried onto poly(methyl-metacrylate) surface. Gaseous ions of lysozyme desorbed from the surface were analyzed using Thermo Finnigan LCQ Duo mass spectrometer. In the spectrum lysozyme ions with 10, 9 and 8 charges (10-times, 9-times, 8-times protonated forms) can be identified.

Figure 6:
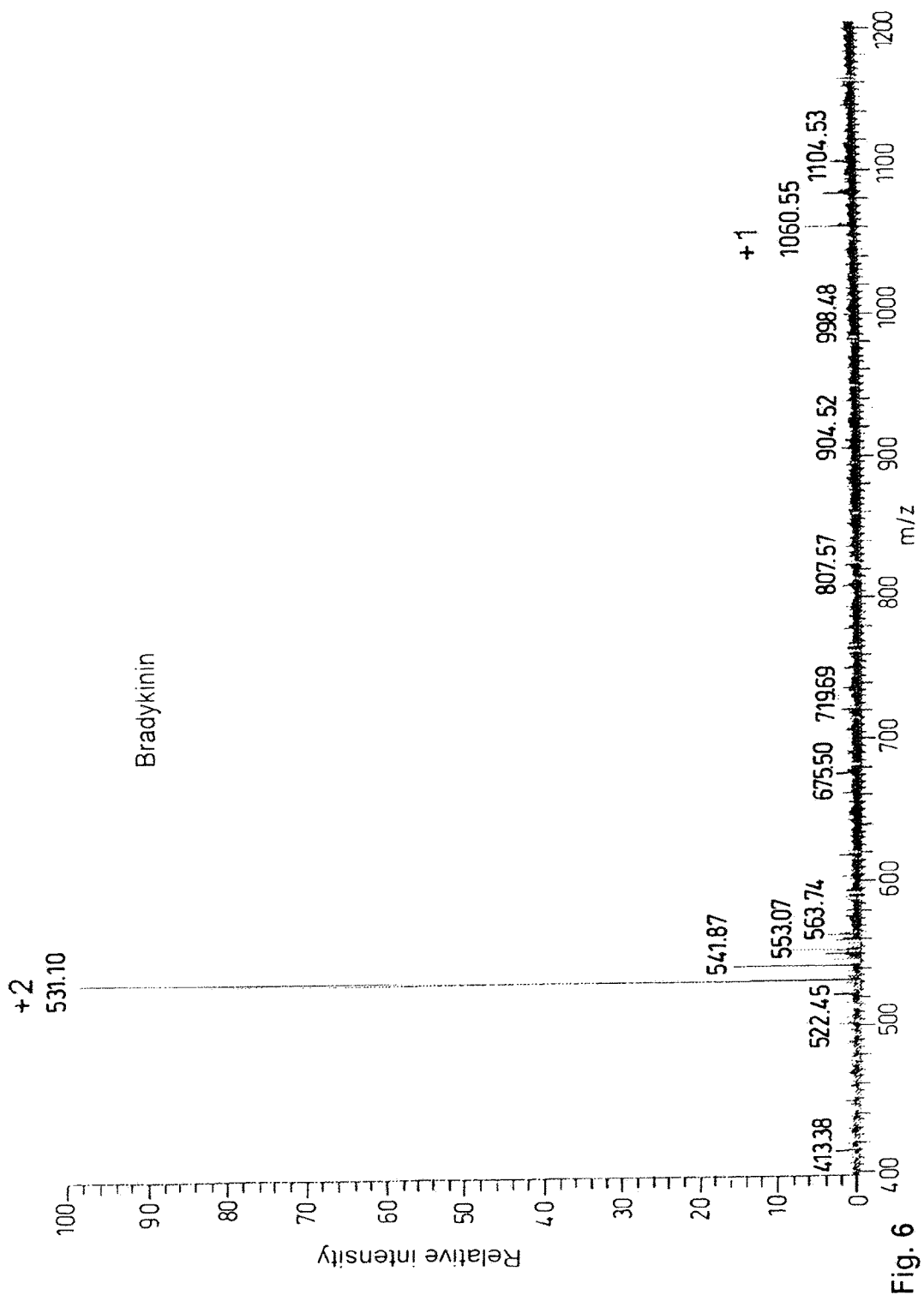

FIG. 6 shows a mass spectrum obtained by apparatus depicted on FIG. 2. 10 µl aqueous solution containing 10 ng bradykinin was dried onto a glass surface. Gaseous ions of peptide desorbed from surface were analyzed using Thermo Finnigan LCQ Duo mass spectrometer. In the spectrum bradykinin ions with 2 and 1 charge/s (single and double protonated forms) and their sodium adducts can be identified.

Figure 7:
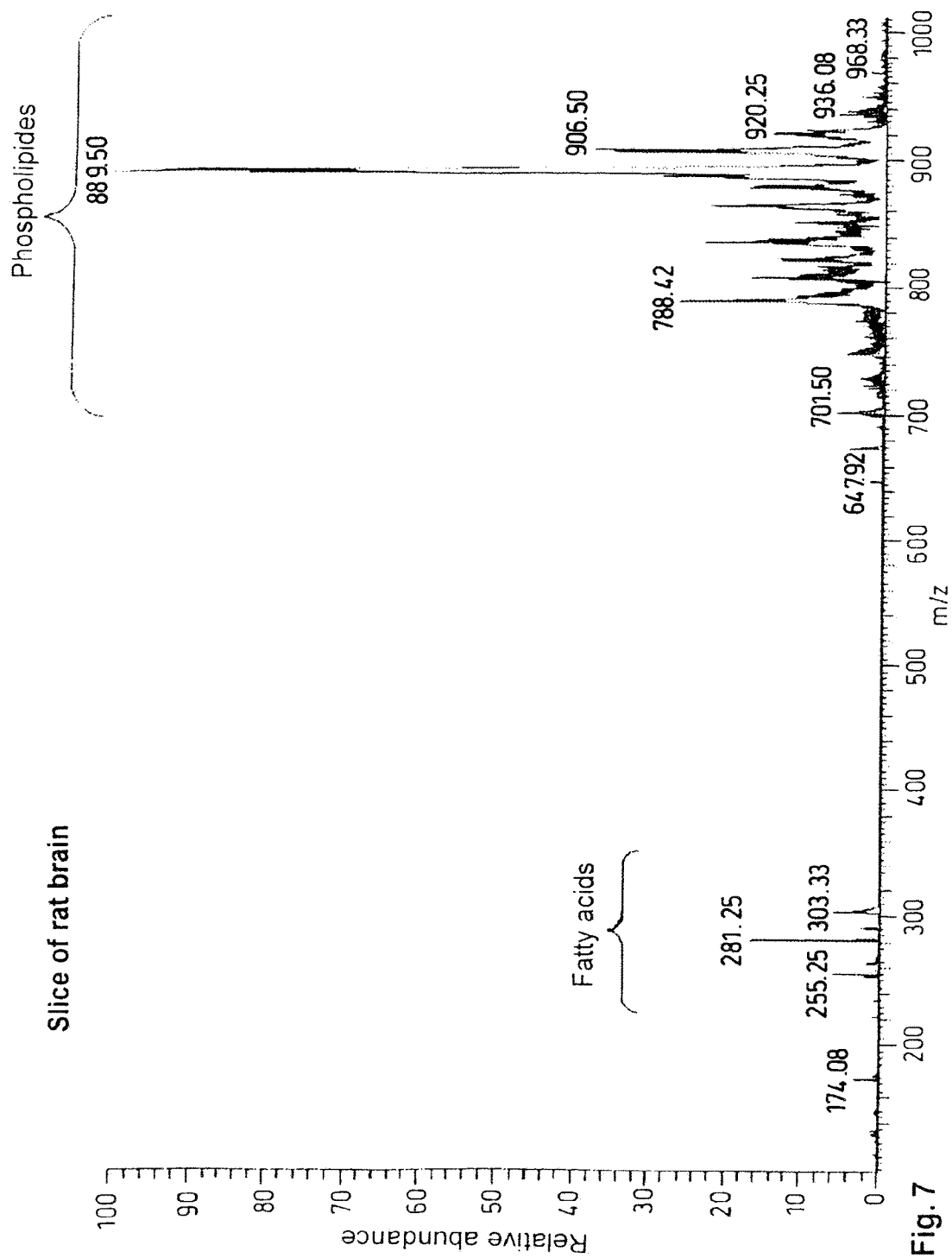

FIG. 7 shows a mass spectrum obtained by apparatus depicted on FIG. 3. 20 µm thick freeze-cut slice of rat brain was deposited onto glass surface. Negative ions of lipid type constituents of the sample were obtained by desorption ionization and analyzed using Thermo Finnigan LCQ Duo mass spectrometer. In the spectrum ions of fatty acids and phospholipids can be identified.

Figure 8:
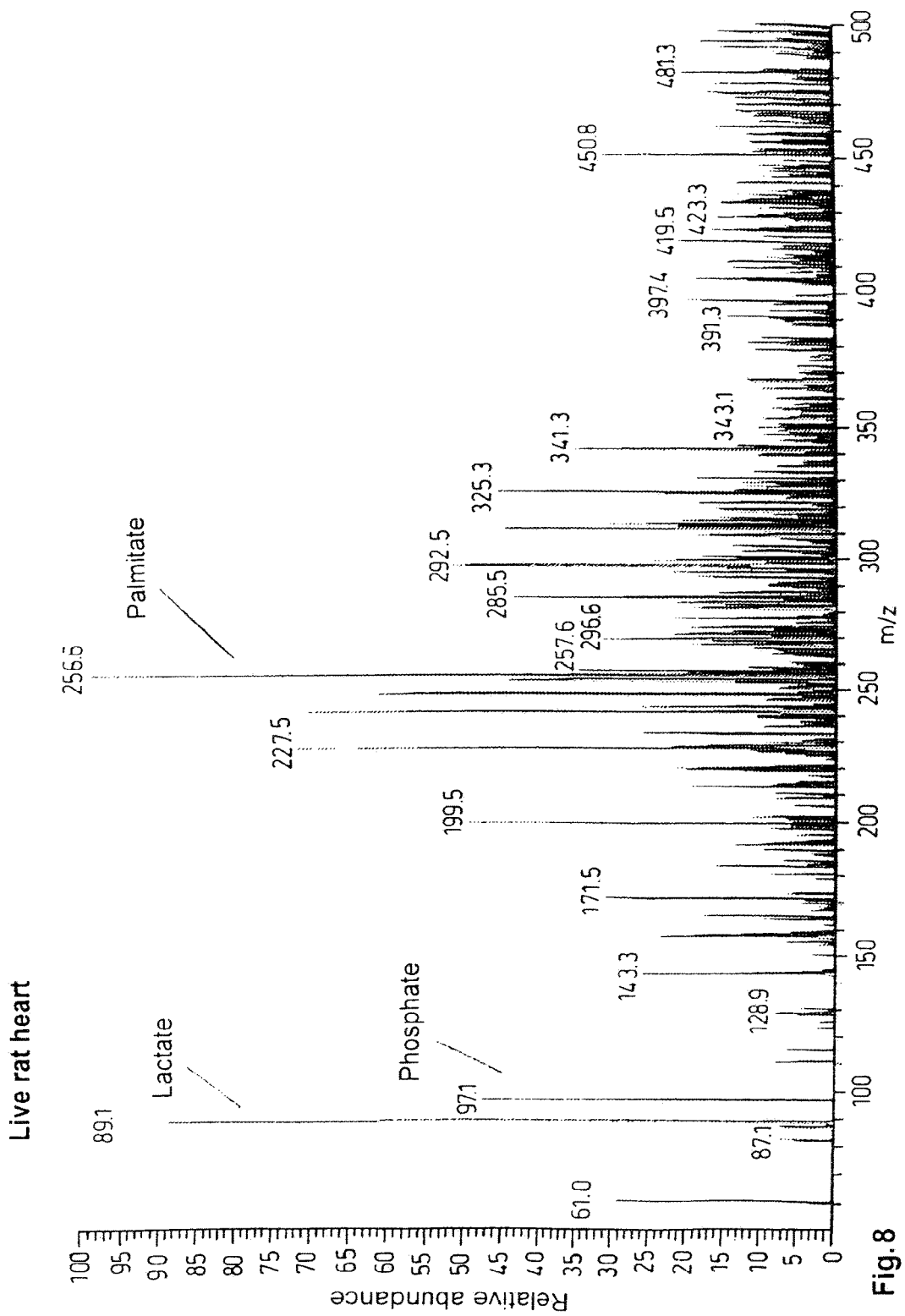

FIG. 8 shows a mass spectrum obtained by apparatus depicted on FIG. 4. Negative ions of components ionized by water jet method from the surface of surgically exposed heart were analyzed using Thermo Finnigan LCQ Duo mass spectrometer. In the spectrum ions can be identified which play key role in the metabolic processes of heart.

EXAMPLES

The method according to the invention is described in details by the following working examples and by references to the figures, without limiting the scope of our claims to them.

Example 1

Water Jet Desorption Ion Source for Mass Spectrometry to Analyze Dried Solvent Solution Droplets 1.1. The Water Jet Desorption Ion Source for Mass Spectrometry Comprises the Following Parts:
HPLC pump (Jasco),
1/16" OD, 1 mm ID stainless steel tube (11),
connectors (Swagelok, Upchurch) (13),
seals (Swagelok, Upchurch) (14),
5 µm ID sapphire nozzle (3),
2 moving stages for 3D linear moving (Newport),
rotating stage for rotation in one dimension (Newport),
high-voltage power supply (Bertan) (4)
HDPE tube, 1/16" OD, 1 mm ID (17),
membrane pump,
mass spectrometer (Thermo Finnigan LCQ Duo).

1.2. Construction of Water Jet Desorption Ion Source for Mass Spectrometry

Schematic drawing of apparatus is shown on FIG. 2. Stainless steel 11 tube is connected to HPLC pump through HDPE tube and 3 nozzle is connected according to FIG. 2. The end of stainless steel tube having the nozzle is mounted on rotating stage utilizing suitable 12 screwed holders, and said rotating stage is mounted onto 3D linear moving stage system in a way that the stainless steel tube is electrically isolated from moving stages. Said moving stage system is mounted on source platform which is mounted onto 9 atmospheric interface part of mass spectrometer by the application of suitable bolts. Electric outlet of 4 high voltage power supply is connected to the stainless steel 11 tube.

Sample carrier plate made of polyethylene is mounted onto another 3 D linear moving stage system by the application of screws. 3D linear moving stage system is also mounted on said source platform in a way that geometric parameters defined on FIG. 2 are set according to values given in Table 1.

HDPE 17 tube used for the removal of excess liquid from the surface is mounted to stainless steel 11 tube in a way that the end of HDPE tube is in 1 mm distance from the nozzle. Distant end (i.e. farther from the sample) of HDPE 17 tube is connected to membrane pump used for said purpose.

1.3. Use of Water Jet Desorption Ion Source for the Investigation of Dried Solvent Droplets Solution phase samples are dropped and dried onto 1 mm thick poly(methyl-metacrylate) 5 surface. Liquid jet directed onto surface is established by pumping 0.1% aqueous acetic acid solution through nozzle by HPLC pump at 10 µl/min flow rate, where the liquid jet emerging from 3 nozzle has an impact angle of 70 degrees to the surface of the sample. Sample and nozzle are positioned in a way that the collection angle, shown on the figure, is 20 degrees. Further experimental details are summarized in Table 1.

TABLE 1

| Parameter | Value |
|---|---|
| Nozzle-to-surface distance | 5 mm |
| Surface-to-mass spectrometer distance | 1 mm |
| Impact angle (15) | 70° |
| Collection angle (16) | 20° |
| High voltage | 4.5 kV |
| MS inlet potential | −6 V |

6 samples deposited and dried onto the surface are studied consecutively by the use of 3D linear moving stage system. FIG. 5 shows mass spectrum of 100 ng bradykinin deposited as drop of solution onto the surface, while FIG. 6 shows mass spectrum of 10 ng cytochrome C deposited as a drop of solution onto surface. Spectra show high similarity to spectra of compounds obtained by electrospray ionization, and the interpretation of spectra is made on the basis of same general rules. Similarity between characters of jet desorption and electrospray spectra is associated with the fact that the de facto ion formation is made from multiply charged droplets. One of the main advantages of jet desorption ionization compared to electrospray is the complete elimination of cross contamination in the case of high-throughput analysis (more than 10 samples per minute).

Example 2

Water Jet Desorption Ion Source for Mass Spectrometry to Define Spatial Distribution of the Concentration of Specific Compounds in a Sample 2.1. Water Jet Desorption Ion Source for Mass Spectrometry to Define Spatial Distribution of Concentration of Specific Compounds in a Sample Comprises the Following Parts:
HPLC pump (Jasco),
1/16" outer diameter, 1 mm internal diameter stainless steel tube, which is sealed on one end by welding in a length of 0.2 mm, and the sealed section is drilled through by means of laser drilling to form a 1 µm diameter circular cross-section orifice (11), connectors (Swagelok, Upchurch) (13),
seals (Swagelok, Upchurch) (14),
2 computer controlled moving stages for 3D linear moving (Newport),
rotating stage for rotation in one dimension (Newport),
high voltage power supply (Bertan) (4),
HDPE 17 tube, 1/16" outer diameter, 1 mm internal diameter,
membrane pump,
mass spectrometer (Thermo Finnigan LCQ Duo).

2.2. Construction of Water Jet Desorption Ion Source to Define Spatial Distribution of Concentration of Specific Compounds in a Sample Schematic drawing of apparatus is shown on FIG. 3. Stainless steel 11 tube, ending in 3 nozzle, is connected to HPLC pump through HDPE tube. The end of the stainless steel tube is mounted on rotating stage, and said rotating stage is mounted onto 3D linear moving stage system in a way that stainless steel tubing is electrically isolated from moving stages. Said moving stage system is mounted on source platform which is mounted onto the atmospheric interface part of mass spectrometer applying suitable bolts. Electric outlet of 4 high voltage power supply is connected to said stainless steel 11 tube.

Sample carrier plate made of polyethylene is mounted onto other 3D linear moving stage system, using appropriate screws. 3D linear moving stage system is also mounted on said source platform in a way that geometric parameters defined on FIG. 2 are set.

HDPE 17 tube used for the removal of excess liquid from surface is mounted in a way that the end of HDPE tube is in 1 mm distance from the nozzle. Distant end (i.e. farther from the sample) of HDPE 17 tube is connected to membrane pump used for said purpose.

2.3. Use of Water Jet Desorption Ion Source to Define Spatial Distribution of Concentration of Specific Compounds in a Sample

6 sample, for example dissections of biological tissues, is mounted onto sample carrier plate and affixed, if required. Working parameters enlisted in Table 2 are set on the apparatus, and sample is moved relatively to nozzle and mass spectrometer as it 19 is shown on FIG. 3 at speed of 10 μm/s. Mass spectra are acquired continuously during the scanning of the surface. Since the 10 to 50 μm thick 18 upper layer of the sample is completely ablated, scanning can be repeated until the sample is completely consumed. Computer controlled motion stage enables the presentation of the collected data against the original position. It enables the determination of the spatial concentration distribution of specific components. FIG. 7 shows mass spectra of rat brain section obtained by the apparatus given on the figure.

TABLE 2

| Parameter | Value |
| --- | --- |
| Nozzle-to-surface distance | 5 mm |
| Surface-to-mass spectrometer distance | 1 mm |
| Impact angle (15) | 90° |
| Collection angle (16) | 20° |
| High voltage | 4.5 kV |
| MS inlet potential | −6 V |

Example 3

Surgical Device Based on Water Jet Desorption 3.1. Surgical Device Based on Water Jet Desorption Comprises the Following Parts (the Device is Shown in FIG. 4):

HPLC pump (Jasco),
1/16" outer diameter, 1 mm internal diameter stainless steel tube (11),
connectors (Swagelok, Upchurch) (13),
seals (Swagelok, Upchurch) (14),
pulled silica capillary nozzle having 1 to 5 μm internal diameter (3),
high voltage power supply (Bertan) (4),
HDPE tube, 1/16" outer diameter, 1 mm internal diameter (17),
membrane pump,
mass spectrometer (Thermo Finnigan LCQ Duo).

3.2. Construction of Surgical Device Based on Jet Desorption

Fused silica capillary having 0.32 mm outer diameter and 10 μm internal diameter is pulled to 1 μm outer diameter at one end (3) and the other end of it is connected to HDPE tube having 1/16" outer diameter which is connected to HPLC pump. Copper tube (20) having lengths of 1 m, 1/8" outer diameter and 2 mm internal diameter is connected to the inlet of mass spectrometer, where the copper tube (20) is equipped with heater (21) and thermometer (22). The heater and the thermometer are connected by electronic temperature controller.

The nozzle, the copper tube connected to the mass spectrometer and the HDPE tube for sucking the surplus water are embedded into holder (19) made of PEEK polymer material.

3.3. Use of Surgical Device Based on Jet Desorption

Switching on the HPLC pump the device is capable for cutting arbitrary soft objects, e.g. biological tissues. Liquid jet forms a cavity (23) on the surface of sample (6) with increasing depth as function of time, as it is shown on FIG. 4, and lateral movement of device cuts the sample object. For producing relevant chemical information by the device about the tissue, parameters enlisted in Table 3 were found to be optimal. FIG. 8 shows mass spectrum recorded by the device on rat heart, in course of a surgical intervention.

TABLE 3

| Parameter | Value |
| --- | --- |
| Nozzle-to-surface distance | 5 mm |
| Surface-to-mass spectrometer distance | 5 mm |
| Impact angle (15) | 90° |
| Collection angle (16) | 40° |
| High voltage | 4.5 kV |
| MS inlet potential | −6 V |

INDUSTRIAL APPLICABILITY

As noted earlier the invention may be utilized in various industrial sectors: chemical industry, environmental analysis, diagnostics, study of biological fluids, tissues, metabolites, marker compounds, tumour markers, general medicine, surgery, study of bacterium/virus markers, drug level identification, study of tissue samples, pharmacology (ADME, toxicology), workplace health/safety, forensic toxicology, pharmaceutical/food industrial toxicology, histology, physiological/biochemical research, material sciences (plastics, composites, metallurgical applications), archaeology (age determination, study of pigments, determination of origin), microbiology (detection of bacteria, fungi form human and natural samples).

LIST OF REFERENCE NUMBERS

A—desorption unit
1—liquid jet

2—liquid
2B—tube for transferring liquid
3—nozzle
4—device for generating electric potential difference
5—surface
6—sample
7—liquid droplets
8—ions or sample particles which are convertible into ions
9—sample collector unit
10—analyser unit
11—tube
12—screwed holder
13—connector
14—seal
15—impact angle
16—collection angle
17—drain tube
18—upper surface of the sample
19—holder
20—tube connected to the analyser unit
20A—outlet of the tube connected to the analyser unit
21—heater
22—thermometer
23—cavity hollowed into the sample

What is claimed is:

1. A method of analyzing a sample, the method comprising:
applying a laser beam to the sample to both cut into the sample a depth of greater than 10 μm and simultaneously convert at least a portion of the sample into gaseous sample particles, wherein the gaseous sample particles comprise gaseous ions and sample particles convertible into gaseous ions;
transporting at least some of the gaseous sample particles to an ion analyzer unit; and
analyzing at least some of the gaseous sample particles with the ion analyzer unit.

2. The method of claim 1, wherein the ion analyzer unit comprises a mass spectrometer or an ion mobility spectrometer.

3. The method of claim 1, further comprising providing results of the analysis in real time to a user, wherein the results indicate an in-depth distribution of a composition of the sample being cut.

4. The method of claim 1, further comprising outputting results of the analysis to generate a chemical image with micrometer scale resolution.

5. The method of claim 1, wherein the applying a laser beam to the sample is performed at atmospheric pressure.

6. The method of claim 1, wherein the applying a laser beam to both cut into the sample and convert at least a portion of the sample into gaseous sample particles permits an in-depth distribution of the composition of the sample across a range of depths.

7. The method of claim 3, wherein providing results of the analysis in real time to a user comprises continuously providing information from results of the analysis to a user.

8. The method of claim 1, further comprising ionizing at least one of the particles convertible into ions between the portion of the sample and the ion analyzer unit.

9. The method of claim 8, wherein the ionizing is performed at atmospheric pressure.

10. The method of claim 8, wherein the ionizing comprises at least one of: corona discharge ionization and secondary electrospray ionization.

11. The method of claim 1, wherein the transporting comprises using a transport tube having a pressure gradient to facilitate transport of the gaseous sample particles to the ion analyzer unit.

12. The method of claim 1, wherein the transporting comprises using a transport tube having an electric potential gradient to facilitate transport of the gaseous sample particles to the ion analyzer unit.

13. A system for analyzing a sample, the system comprising:
a device configured to apply a laser beam to both cut into the sample a depth of greater than 10 μm and simultaneously convert at least a portion of the sample into gaseous sample particles, wherein the gaseous sample particles comprise gaseous ions and sample particles convertible into gaseous ions;
a sample collector unit configured to transport the gaseous sample particles from the sample to an ion analyzer; and
an ion analyzer operationally coupled to the sample collector unit, the ion analyzer configured to generate data for identifying components of the sample.

14. The system of claim 13, wherein the ion analyzer comprises a mass spectrometer or an ion mobility spectrometer.

15. The system of claim 13, wherein the device is configured to convert at least a portion of the sample into gaseous sample particles at a pressure higher than vacuum.

16. The system of claim 13, wherein the device is configured to simultaneously cut into the sample and convert at least a portion of the sample into gaseous sample particles and thereby to determine and provide an in-depth distribution of a composition of the sample being cut.

17. The system of claim 16, wherein the ion analyzer is configured to continuously generate data corresponding to a composition of the sample and provide information regarding the composition of the sample to a user in substantially real time.

18. The system of claim 13, further comprising a secondary ionization device configured to ionize the sample particles convertible into ions between the sample and the ion analyzer.

19. The system of claim 18, wherein the secondary ionization device comprises at least one of: a corona discharge ionization device and a secondary electrospray ionization device.

20. The system of claim 13, wherein the sample collector unit comprises a transport tube having a pressure gradient to facilitate transport of the gaseous sample particles to the ion analyzer.

21. The system of claim 13, wherein the sample collector unit comprises a transport tube having an electric potential gradient to facilitate transport of the gaseous sample particles to the ion analyzer.

22. A method for analyzing a sample, the method comprising:
applying a laser beam to cut into the sample a depth of greater than 10 μm, wherein the laser cuts by forming a cavity on the surface of the sample with an increasing depth as a function of time;
dislocating ions and sample particles convertible into ions from the sample using the laser beam;
converting at least a portion of the sample into gaseous ions by other than solvent action; and
analyzing the obtained gaseous ions.

23. The method of claim 1, further comprising controlling a temperature of the sample during the applying step, the controlling includes one or more of externally heating the sample up to 300° C. and externally cooling the sample down to about −50° C.

24. The method of claim 1, further comprising:
continuously acquiring mass spectra produced as a result of the analyzing step; and
reporting at least one feature of the mass spectra to a user in about real time indicative of the chemical composition of the sample being cut by the laser.

* * * * *

UNITED STATES PATENT AND TRADEMARK OFFICE
CERTIFICATE OF CORRECTION

PATENT NO. : 9,709,529 B2
APPLICATION NO. : 13/680329
DATED : July 18, 2017
INVENTOR(S) : Zoltán Takáts Page 1 of 1

It is certified that error appears in the above-identified patent and that said Letters Patent is hereby corrected as shown below:

On the Title Page

Item (54), (Title) at Lines 1-3, Change "METHOD AND DEVICE FOR IN VIVO DESORPTION IONIZATION OF BIOLOGICAL TISSUE" to --METHOD AND DEVICE FOR DESORPTION IONIZATION--.

In the Specification

In Column 1 at Lines 1-3, Change "METHOD AND DEVICE FOR IN VIVO DESORPTION IONIZATION OF BIOLOGICAL TISSUE" to --METHOD AND DEVICE FOR DESORPTION IONIZATION--.

Signed and Sealed this
Twenty-first Day of November, 2017

Joseph Matal
*Performing the Functions and Duties of the
Under Secretary of Commerce for Intellectual Property and
Director of the United States Patent and Trademark Office*